US005476647A

United States Patent [19]

Chow et al.

[11] Patent Number: 5,476,647
[45] Date of Patent: Dec. 19, 1995

[54] COMPLEX CALCIUM AND FLUORIDE CONTAINING MOUTH RINSES, DENTIFRICES, AND CHEWABLE TABLETS

[75] Inventors: Laurence C. Chow, Potomac; Shozo Takagi, Gaithersburg, both of Md.

[73] Assignee: American Dental Association Health Foundation, Chicago, Ill.

[21] Appl. No.: 120,856

[22] Filed: Sep. 13, 1993

[51] Int. Cl.$^6$ ................................ A61K 7/16; A61K 7/18
[52] U.S. Cl. ...................... 424/52; 106/35; 433/199.1; 433/215; 433/222.1; 433/228.1
[58] Field of Search ................................ 424/52; 106/35; 433/199.1, 215, 228.1, 222.1

[56] References Cited

U.S. PATENT DOCUMENTS

| | | | |
|---|---|---|---|
| Re. 33,161 | 2/1990 | Brown et al. | 433/199.1 |
| Re. 33,221 | 5/1990 | Brown et al. | 433/199.1 |
| 3,913,229 | 10/1975 | Driskell | 433/215 |
| 3,943,267 | 3/1976 | Randol | 424/49 |
| 4,048,300 | 9/1977 | Thomlinson et al. | 424/52 |
| 4,080,440 | 3/1978 | DiGuilio | 424/49 |
| 4,083,955 | 4/1978 | Grabenstetter | 424/52 |
| 4,098,435 | 7/1978 | Weyn | 222/94 |
| 4,108,980 | 8/1978 | Duff | 424/52 |
| 4,177,258 | 12/1979 | Gaffar et al. | 424/52 |
| 4,183,915 | 1/1980 | Gaffar | 424/52 |
| 4,283,385 | 8/1981 | Dhabhar et al. | 424/52 |
| 4,342,741 | 8/1982 | Aoki | 424/49 |
| 4,358,381 | 9/1982 | Gaffar | 424/52 |
| 4,363,795 | 12/1982 | Wahlstam | 424/49 |
| 4,397,837 | 8/1983 | Raaf et al. | 424/52 |
| 4,405,600 | 9/1983 | Besic | 424/57 |
| 4,460,565 | 7/1984 | Weststrate | 424/52 |
| 4,515,770 | 5/1985 | Besic | 424/49 |
| 4,518,430 | 5/1985 | Brown et al. | 433/228.1 |
| 4,532,124 | 7/1985 | Pearse | 424/52 |
| 4,556,561 | 12/1985 | Brown et al. | 424/48 |
| 4,606,912 | 8/1986 | Rudy et al. | 424/52 |
| 4,610,873 | 9/1986 | Rudy et al. | 424/52 |
| 4,612,053 | 9/1986 | Brown et al. | 433/201.1 |
| 4,714,608 | 12/1987 | Rölla | 424/52 |
| 4,837,007 | 6/1989 | Duckworth et al. | 424/52 |
| 4,861,590 | 8/1989 | Grodberg | 424/602 |
| 4,880,610 | 11/1989 | Constantz | 606/53 |
| 4,923,683 | 5/1990 | Sakuma et al. | 424/52 |
| 4,990,327 | 2/1991 | Neirinckx | 424/52 |
| 5,034,059 | 7/1991 | Constantz | 424/423 |
| 5,037,639 | 8/1991 | Tung | 424/57 |
| 5,047,031 | 9/1991 | Constantz | 606/77 |
| 5,053,212 | 10/1991 | Constantz et al. | 433/199.1 |
| 5,129,905 | 7/1992 | Constantz | 606/76 |
| 5,145,668 | 9/1992 | Chow et al. | 424/52 |
| 5,320,830 | 7/1994 | Lukacovic et al. | 424/52 |

FOREIGN PATENT DOCUMENTS

| | | |
|---|---|---|
| 0089136A | 9/1983 | European Pat. Off. . |
| 0263638A2 | 4/1988 | European Pat. Off. . |
| WO9010435A | 9/1990 | European Pat. Off. . |
| WO9204006A | 3/1992 | European Pat. Off. . |

OTHER PUBLICATIONS

Tung, et al., "Hydrolysis of Dicalcium Phosphate Dihydrate In The Presence Or Absence Of Calcium Fluoride" Basic Biological Sciences; Dent. J. Res. 64(1):2–5.

Patel, P. R., et al. "Solubility of $CaHPO_4 \times 2H_2O$ In the Quaternary System $Ca(OH)_2-H_3PO_4-NaCl-H_2O$ at 25° C." J.Res. Nat. Bur. Stand.–78A:675–681 (19.

Brown, W., et al. "Crystallography Of Tetracalcium Phosphate" J.Res. Nat. Bur Stand. 69A 547–551 (1965).

Moreno, E. et al., "Stability of Dicalcium Phosphate Dihydrate in Aqueous Solutions and Solubility of Octocalcium Phosphate" Soil Science Society Proceedings 1960.

McDowell, et al. "Solubility of $Ca_5(PO_4)_3 \times$ In the System $Ca(OH)_2-H_3PO_4-H_2O$ at 5°, 15°, 25° and 37° C." J. Res. Nat. Bur. Stand.—81A: 273–281 (1977).

Gregory, T. M. et al., "Solublility of $B-Ca_3(PO_4)_2$ in the System $Ca(OH)_2-H_3PO_4$ at 5°, 15°, 25° and 37° C." J. Res. Nat. Bur. Stand.—78A: 667–674 (1974).

Gregory, T. M., et al. "Solublility of $CaHOP_4 \times 2H_2O$ in the System $Ca(OH)_2-H_3PO_4-H_2O$ at 5°, 15°, 25°, and 37.5° C." J.Res. Nat. Bur. Stand. 74A:461–475 (19.

Driskell, et al. "Development of Ceramic and Ceramic Composite Devices for Maxillofacial Applications" J. Biomed. Mater. Res. Symposium 6: 345–361 (1972.

Levine, R. S., et al. "Remineralisation of Natural Carious Lesions Of Enamel In Vitro" Brit. dent. J. 1974: 137, 132, Dental Caries Dental Enamel: Hydroxy apatite: 132–134.

Zimmerman, et al. "The Effect of Remineralization Fluids On Carious Lesions In Vitro" Brit. dent. J., 1974: 137, 132, Dental Caries Dental Enamel: Hydroxyapatite: 132–134.

Silverstone, et al. "Progressions of Caries–like Lesions In Vitro After Exposure To Synthetic Calcifying Fluids" IADR Abstract No. 283 (1979).

Wefel, J. S., et al. "Artificial Lesion Formation In TiF4 and APF Treated Enamel" IADR Abstract No. 284 (1979).

Crall, J. J. et al., "Artificial Lesion Formation and Progression after Two–step Topical Fluorides" IADR Abstract No. 285 (1979).

Hiatt, W. H. et al. "Root Preparation I. Obturation of Dentinal Tubules In Treatment Of Root Hypersensitivity" J. Periodontal: 373:380 (1972).

(List continued on next page.)

*Primary Examiner*—Ronald W. Griffin
*Attorney, Agent, or Firm*—Banner & Allegretti, Ltd.

[57] ABSTRACT

The present invention relates to compositions and methods for fluoridating teeth. More specifically, the invention is a reactive, multi-component composition consisting of an admixture of a stable, non-toxic soluble calcium salt and a soluble calcium complexing (chelating) agent, with a stable, non-toxic soluble fluoride compound, a buffer, and one or more non-interfering carriers. The components of this admixture are mixed in an aqueous environment, resulting in a controlled precipitation of calcium fluoride, and then promptly applied to the tooth surfaces. The invention contemplates mouth rinses, dentifrices, gels, and chewable tablets for application of these compositions and methods.

30 Claims, 2 Drawing Sheets

OTHER PUBLICATIONS

Gelhard, T. B. F. M., "Rehardening Of Artificial Enamel Lesions In Vitro" Caries Res. 13: 80–83 (1979).

Silverstone, "Remineralization Phenomena" Caries Res. II (Suppl. 1): 59–84 (1977).

Briner, W. W., "Significance Of Enamel Remineralization" 53 239–243 (19784).

NASA And Dentristry, "New–Tooth Enamel From Brushite Crystals" (Oct. 1977).

Pickel, F. D. "The Effects Of A Chewing Gum Containing Dicalcium Phosphate On Salivary Calcium And Phosphate" Ala. J. Med Sci. 2: 286–87 (1965).

Trautz, "Crystallographic Studies Of Calcium Carbonate Phosphate" Annals of the N.Y. Acad. Sci. 35, Article 1: 145–160 (1960).

Blumenthal, N. C. et al. "Effect Of Preparation Conditions On The Properties And Transformation Of Amorphous Calcium Phosphate" Mat. Res. Bull. 7: 1181–1190 (1972).

Posner, A. S., et al. "Synthetic Amorphous Calcium Phosphate And Its Relation To Bone Mineral Structure" Accts. Of Chem. Res. 8: 273–281 (1975).

Tung, M. S. et al. "An Intermediate State In Hydrolysis Of Amorphous Calcium Phosphate" Calcif Tissue Int 783–790 (1983).

LaGeros, R. Z. "Apatitic Calcium Phosphates: Possible Dental Restorative Materials" IADR Abstract No. 1482 J. Dent. Res. 61 (1982).

Tung M. S. et al. "The Effects of Calcium Phosphate Solutions on Permeability of Dentin": J. Dent. Res. 65 Abstract No. 167 (1986).

Brown, et al. "Singular Points in the Chemistry of Teeth" IADR Abstract No. 12 J. Dent. Res. 54: 74 (1975).

Guide to Dental Materials and Devices, 7 Ed. p. 49 (ADA 1974).

Aboba Takaaki, et al., "Small–Angle X–Ray Scattering Study On The Transformation Of Amorphous Calcium Phosphate To Crystalline Apatite" Chem. Abstracts, vol. 91 No. 13, Abstract No. 105934q, (1979).

Ababa Takaaki, "X–Ray Diffraction Study On The Amorphous And Crystalline Components In Bone Mineral" Chem. Abstracts, vol. 91 No. 13, Abstract No. 105935r, (1979).

Termine, John D., et al. "Calcium Phosphate In Vitro" Chem. Abstracts, vol. 73, Abstract No. 12698–a, (1970).

Hong, Y. C. et al. (1989): "The Periapical Tissue Reactions to a Calcium Phosphate Cement in the Teeth of Monkeys," J. Dent. Res. (Submitted).

McDowell et al., "Solubility Study of Calcium Hydrogen Phosphate. Ion Pari Formation," Inorg. Chem. 10:1638–1643 (1971).

Tung, et al., "Effects of Calcium Phosphate Solutions on Dentin Permeability". vol. 19 No. 8, J. of Endodontic (1983).

Brown, "Solubilities of Phosphates and Other Sparingly Soluble Compounds" from Griffith et al., Environmental Phosphorous Handbook (John Wiley & Sons, New York 1973).

De Rijk, et al. (1986): Clinical Evaluation of an Hydroxyapatite Precipitate for the Treatment of Dentinal Hypersensitivity, *Biomedical Engineering V. Recent Developments,* Proc of 5th Southern Biomedical Engineering Conference. Subrata Saha, Ed., New York: Pergamon Press, pp. 336–339.

Lu, et al., (1988): New Attachment Following The Use of a Novel Calcium Phosphate System, J. Dent Res. 67:352, Abst. No. 1913.

Schreiber, et al. (1988): Remineralization of Root Caries Lesion by a Calcium Phosphate Slurry, J. Dent. Res. 67: Abst. No. 255.

Sugawara et al, (1987): A Calcium Phosphate Root Canal Sealer–Filler J. Dent. Res. 66:296 Abst. No. 1516.

Sugawara et al., (1989): "Formation of Hydroxyapatite in Hydrogels from Tetracalcium Phosphate/Dicalcium Phosphate Mixtures," *J.Nihon Univ. Sch. Dent.* vol. 31, No. 1 pp. 372–381.

Matsuya, et al. "Effects of pH on the Reactions of Tetracalcium Phosphate and Dicalcium Phosphate," IADR Abstract 1991.

Chow and Takagi, (1991): "Deposition of Fluoride On Tooth Surfaces By a Two Solution Mouth Rinse *In Vitro,*" *Caries Res.* 25: 397–401.

Vogel, et al., (1992): "*In Vivo* Fluoride Concentration Measured for Two Hours After a NaF as a New Two–Solution Rinse," *J. Dent. Res.* 71: 488–452.

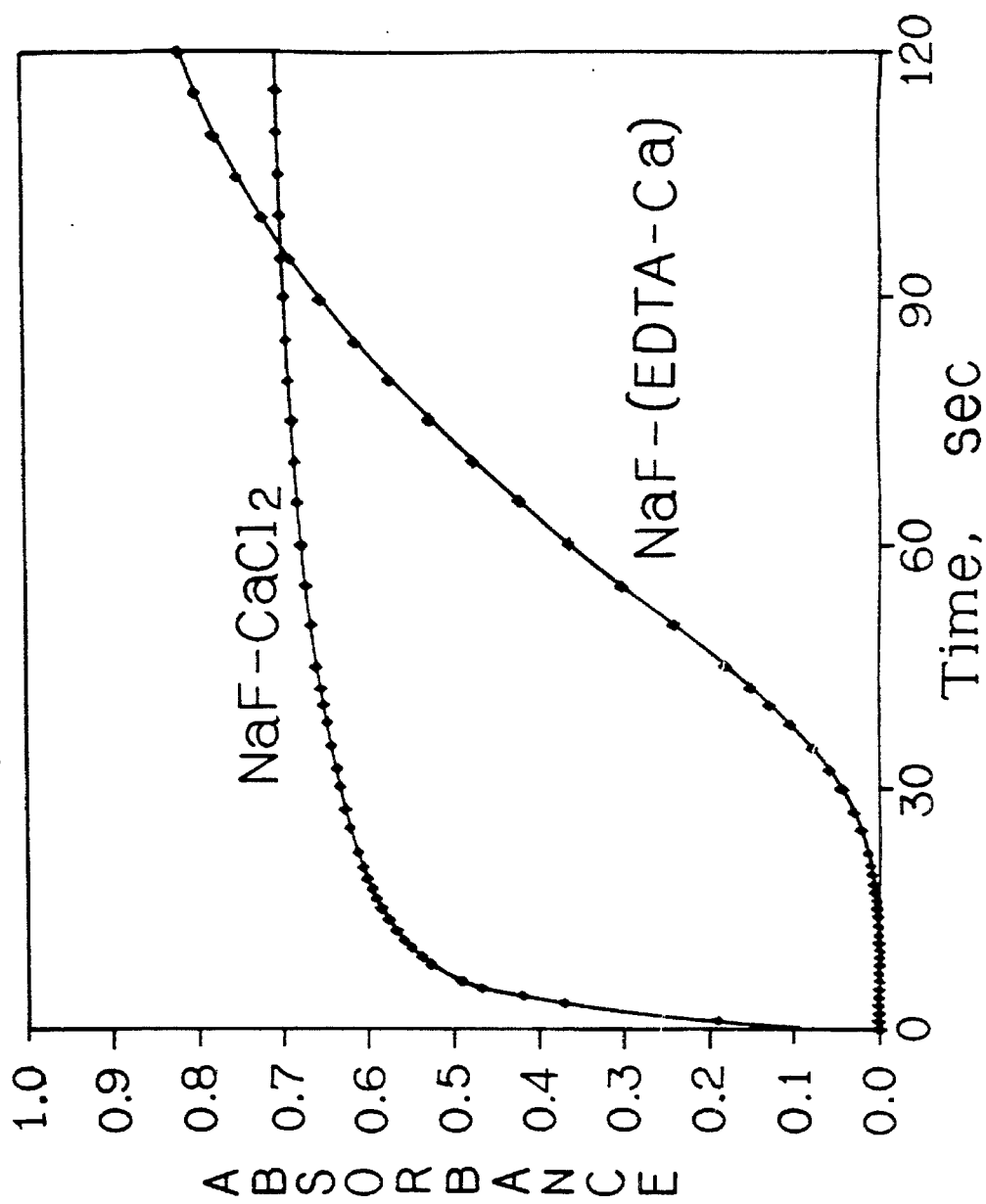

COMPLEX CALCIUM AND FLUORIDE CONTAINING MOUTH RINSES, DENTIFRICES, AND CHEWABLE TABLETS

This invention was supported in part by research grant number DE05354 to the American Dental Association Health Foundation from the National Institute of Dental Research. The Government has certain rights in this invention.

BACKGROUND OF THE INVENTION

Self-applied fluorides in the forms of mouth rinses and dentifrices are widely used in this country and elsewhere in the world. They have been shown to be effective in reducing tooth decay. The fluoride containing mouth rinses formulated for daily use usually contain 250 parts per million (ppm) of fluoride as sodium fluoride or stannous fluoride. The fluoride dentifrices typically contain 1000 ppm of fluoride as sodium fluoride or sodium monofluorophosphate. The carlostatic effects of both of these fluoride regimens are believed to derive from their ability to deposit fluoride on the surfaces of teeth and other tissues in the mouth. Although the deposited fluoride is labile in nature and is easily leached out of teeth and mouth tissues, the daily application of either the rinse or dentifrice can produce and maintain an elevated level of fluoride in the mouth.

U.S. Pat. No. 4,556,561 discloses solutions, gels, and substantially nonaqueous dispersions that form dicalcium phosphate dihydrate under appropriate conditions, as well as methods of their use. These compositions are useful in topically fluoridating and/or mineralizing dental tissue, such as enamel, dentin, and exposed root surfaces. The incorporated fluoride is in the form of $Ca_5(PO_4)_3F$ and is more permanently retained than $CaF_2$ and other fluoridation products.

U.S. Pat. No. 4,048,300 discloses a single dental preparation including a material containing calcium and phosphorous. The calcium/phosphorous containing component may also include fluoride. Examples of calcium/phosphorous/fluoride components include fluorapatite, fluorohydroxyapatite, apatite, calcium deficient apatite, and hydroxyapatite substituted by a fluoranion. This component is useful in a dental cream.

U.S. Pat. No. 4,080,440 discloses a method for the remineralization of tooth enamel using a two solution system. The first solution is a cationic solution containing a calcium salt and optionally a heavy metal cation. The second solution is an anionic solution containing a phosphate salt and optionally non-phosphatic anions including fluoride ions. The pH of the solutions ranges from 2 to 4 and the ratio of calcium to phosphorous ranges from 0.01 to 100. The solution, produced by mixing the two-components, is described as a "metastable" solution and requires a residence time in the mouth of from 10 seconds to about 3 minutes in order to raise the pH of the solution such that the components of the solution precipitate in the tooth resulting in enamel remineralization.

U.S. Pat. No. 4,083,955 describes a two-step process for remineralizing dental enamel. In the process, two solutions, one comprising a calcium salt, and the other solution comprising a phosphorous salt along with an optional fluoride salt, are sequentially contacted with dental enamel. The sequential solution contact results in the surface of the enamel being remineralized.

U.S. Pat. No. 4,108,980 describes a process for applying fluoride to teeth with a material having calcium and phosphate components. The dental material includes a salt which ionizes to produce fluoride ions. The formulations described in this invention are made well in advance of application to tooth surfaces.

U.S. Pat. Nos. 4,177,258 and 4,183,915 describe stable solutions for dental remineralization. The solutions include a source of calcium ions, a source of phosphate ions and a source of fluoride. The solutions also include an anti-nucleating agent consisting of diamine tetramethylenephosphonic acids having a specific formula. The anti-nucleating agent stabilizes the calcium ions and phosphorous ions and prevents them from precipitating as large, insoluble apatite crystals by absorbing onto spherical nucleated particles as they form and blocking crystal growth.

U.S. Pat. No. 4,348,381 describes solutions similar to those described in the '258 and '915 patents above. However, the anti-nucleating agent of the '381 solution is PBTA and its water soluble salts.

U.S. Pat. No. 4,397,837 describes a two-phase dental composition in which the two phases are combined when applied to teeth. The first phase of the composition includes a calcium component. The second phase includes a water soluble phosphate component and a water soluble fluoride component.

U.S. Pat. No. 4,460,565 describes a remineralizing dentifrice composition. The composition includes a calcium containing component, two fluoride components, an alkali or alkaline earth metal fluoride and an alkali metal fluorophosphate, two phosphate components, a soluble cyclic alkali metal phosphate and a soluble linear phosphate.

U.S. Pat. No. 4,532,124 describes a dental rinse. The dental rinse includes water soluble salts of fluorine, calcium and phosphorous. The composition additionally includes a substance metabolized into an alkali, such as urea, which raises the solution pH causing calcium precipitation.

U.S. Pat. Nos. 4,606,912 and 4,610,873 describe a clear, stable aqueous mouthwash free of calcium phosphate crystals. The mouthwash includes a chelating agent in combination with a calcium ion source, and a phosphate ion source. The calcium ion source consists of a component capable of providing fluoride ions. The aqueous composition contains calcium ions, phosphate ions, and fluoride ions.

U.S. Pat. No. 4,714,608 describes an aqueous dental preparation. The dental preparation includes a fluoride component in a solution having a pH less than 2. The compound can be applied to teeth either before or after the teeth are treated with calcium. This provides for the precipitation of $CaF_2$ as a thin homogeneous layer on the tooth enamel.

U.S. Pat. No. 4,861,590 describes a sustained release fluoride in calcium composition. The composition includes MFP (monofluorophosphate) and an ionizable calcium source. Sodium fluoride may be added to the composition as desired.

U.S. Pat. No. 4,283,385 describes dentifrices containing insoluble calcium compounds utilized as abrasive dentifrices with a minor amount of EDTA or its sodium salts. Also included in this single component dentifrice is a fluoride compound, preferably sodium monofluorophosphate.

It has also been demonstrated that a 1-minute rinse application with a sodium fluoride rinse that contained 250 ppm of F deposited $0.34/\mu g/cm^2$ of F, and a 1-minute brushing with a NaF dentifrice that contained 1000 ppm of F deposited 0.25 $\mu g/cm^2$ of F on the tooth surface. Chow, L. C. and Takagi, S. (1991): Deposition of Fluoride on Tooth Surfaces by a Two-solution Mouth Rinse in vitro. Caries Res, 25:397–401. Based on the recommended quantity for the rinse (10 ml) or for the dentifrice (1 gram) per application and the total surface area of the teeth in the mouth, it was estimated that less than 0.5% of the F in the rinse or the dentifrice is deposited on the teeth. Some of the F is also deposited in the plaque and soft tissue surfaces, but the bulk of the F contained in the rinses or dentifrices is presumably expectorated (a small fraction of F is also swallowed). A major reason for this very low yield of F retention is the lack of a reaction mechanism for the F in the rinse or dentifrice to precipitate out during the short application time.

U.S. Pat. No. 5,145,668 (Chow and Takagi) discloses a system comprised of two components (solutions or pastes) which when brought in contact, generate a rapid but controlled reaction that precipitates calcium fluoride continuously within the 1-minute time. Component A contains a soluble calcium salt (e.g., $CaCl_2$) and a pH buffer (sodium acetate), and component B contains a complex F compound (e.g., $Na_2SiF_6$). Each component is stable for indefinite periods in the absence of the other. When the two components are combined, hydrolysis of the complex F compound will occur, which produces sufficient amounts of free F to cause calcium fluoride precipitation. This in turn keeps the free F concentration in the mixture sufficiently low to allow continued hydrolysis of the complex F compound and precipitation of calcium fluoride. The H+ions, a byproduct of the complex F hydrolysis, are consumed by the pH buffer so that the pH of the rinse would remain near neutral. With proper concentrations of calcium and complex F in the two solutions, a significant amount of calcium fluoride can be deposited on the tooth surface within the 1-minute application time. The chemical reactions that occur in the two-component system may be described by the following equations:

$$SiF_6^{2-} + 2H_2O \rightarrow SiO_2 + 6F^- + 4H^+ \quad (1)$$

$$3Ca^{2+} + 6F^- \rightarrow 3CaF_2 \quad (2)$$

The efficacy of this two-component system has been demonstrated in studies published in the scientific literature. Chow, L. C. and Takagi, S. (1991): Deposition of Fluoride on Tooth Surfaces by a Two-solution Mouth Rinse in vitro. Caries Res, 25:397–401; Chow, L. C., Takagi, S., and Shih, S. (1992): Effect of a Two-solution Fluoride Mouthrinse on Remineralization of Enamel Lesions in vitro J. Dent. Res., 77:443–447; Vogel, G. L., Mao, Y., Carey, C. M., Chow, L. C. and Takagi, S. (1992): in vivo Fluoride Concentrations Measured for Two Hours After a NaF or a New Two-solution Rinse. J. Dent. Res. 71:448–452.

SUMMARY OF THE INVENTION

One significant disadvantage of the two-component F system described above is that it requires the use of a complex F compound that has a specific hydrolytic property. The compounds known to be suitable for this purpose include the salts of fluorosilisic acid ($H_2SiF_6$) and fluorostannic acid ($H_2SnF_6$). Because none of the suitable complex F salts are currently approved by the U.S. Food and Drug Administration for use in rinses, dentifrices, and other oral health care products, a great investment of expense and effort would be required to demonstrate safety in addition to efficacy before these F compounds may be used clinically. Investigation of a two-component system composed of $NaF-CaCl_2$, which also readily precipitates calcium fluoride, demonstrates that it is nonetheless ineffective in producing a high F deposition.

It has now been discovered by the inventors that the increased F deposition achieved by the two-component system of Chow and Takagi described above may also be attained with the use of a different novel two-component system. Component A of the system contains a soluble calcium source and a soluble Ca-complexing anion such as ethylene diaminetetraacetic acid (EDTA). The calcium in this phase is partially bound to the Ca-complex agent. Component B contains an FDA approved F compound such as sodium fluoride or stannous fluoride. When the two components are combined, precipitation of calcium fluoride ($CaF_2$) removes free $Ca^{2+}$ from the solution. This leads to the release of additional free $Ca^{2+}$ from the calcium binding agent which, in turn, allows additional $CaF_2$ to precipitate. The release of $Ca^{2+}$ from the EDTA-Ca complex can be further increased by decreasing the pH of the solution such that the dominant EDTA species at the lower pH is a weaker Ca complexing agent than the EDTA at the original pH (see equation 5 below).

Thus, the chemical reactions that occur in this two-component system may be represented by the following equations:

$$Ca^{2+} + 2F^- \rightarrow CaF_2 \quad (3)$$

$$CaH(EDTA)^- \rightarrow Ca^{2+} + H(EDTA)^{3-} \quad (4)$$

$$CaH(EDTA)^- \rightarrow Ca^{2+} + H_2(EDTA)^{2-} \quad (5)$$

It is an object and advantage of the present inventive system, that when used in the form of mouth rinses, dentifrices, gels, or chewable tablets, it can deposit significantly more fluoride in the mouth than presently commercialized formulations containing comparable amounts of fluoride. Thus, the new formulations based on this two-component system should be significantly more efficacious than those currently in use.

It is an additional object and advantage of this invention to preferably employ calcium and fluoride sources for dental fluoridation which are relatively readily available and amenable to regulatory approval.

It is a further object and advantage of the present invention to provide a system of rapid yet controlled precipitation of active fluoride onto and into the teeth. Through the use of the present invention incorporating a Ca-complexing anion the amount of calcium available to react with the fluorine at any given time is controlled. As a result controlled continuous precipitation occurs providing effective deposition of fluoride on the teeth.

Also, since none of the currently used fluoride agents contain soluble calcium in the formulation, the calcium in the $CaF_2$ formed on the tooth surfaces is derived from the tooth mineral; i.e., a small amount of the tooth mineral is dissolved with each application, and some of the dissolved calcium is reprecipitated in the form $CaF_2$. In contrast, the inventive compositions, which always contain appropriate amounts of calcium, can supply the calcium needed to form $CaF_2$. Thus, the treatment reaction does not require dissolution of the tooth mineral, and no loss of tooth mineral is expected even with frequent and protracted applications.

More specifically, in accordance with the invention, the rinse or dentifrice is generally formulated in the form of two separate phases (liquids, gels, or pastes) which will be combined just before the application. Each phase is stable for indefinite periods in the absence of the other. Shelf stability of a tablet-type product can be enhanced by protecting it from contact with moisture before use. When the two phases are combined, precipitation of calcium fluoride will occur. This removes the free calcium from the solution, which, in turn, leads to the release of more calcium ions from the calcium complexing agent. With proper concentrations of complexed calcium and fluoride in the two solutions, a significant amount of calcium fluoride can be deposited on the tooth surface in a controlled manner within a typical application time.

Thus, the present invention includes a method for fluoridating teeth comprising (1) mixing in an aqueous environment a first component comprising a stable, non-toxic soluble calcium salt and a soluble calcium complexing agent with a second component comprising a stable, non-toxic soluble fluoride compound, resulting in precipitation of calcium fluoride, followed by (2) prompt application of the mixture to tooth surfaces. The invention also contemplates mouth rinses, dentifrices, gels, and chewable tablets for application of the above-described compositions.

In one embodiment, this invention is a method for fluoridating teeth with a reactive, multi-component composition. The method comprises mixing, in an aqueous environment, a first component consisting of a stable, non-toxic soluble calcium salt and a soluble calcium complexing agent in a non-interfering carrier, with a second component consisting of a stable, non-toxic soluble fluoride compound, in a non-interfering carrier. The first component, the second component, or both the first and second component further include a buffer. The mixture defines a reactive, multi-component composition wherein calcium fluoride is precipitated from the reactive multi-component composition upon mixing. Next, the reactive, multi-component composition is applied to tooth surfaces. Once mixed, the reactive multi-component composition is preferably applied to tooth surfaces for a period of time ranging from about 10 seconds to about 4 minutes.

In another embodiment, this invention is a reactive, multi-component composition consisting of an admixture of a stable, non-toxic soluble calcium salt and a soluble calcium complexing (chelating) agent, with a stable, non-toxic soluble fluoride compound, a buffer, and one or more non-interfering carriers. The reactive multi-component composition preferably has a useful life of from about 4 minutes to about 4 hours or longer.

In yet another embodiment, this invention is a reactive, multi-component composition consisting of an admixture of a stable, non-toxic soluble calcium salt and a soluble calcium complexing (chelating) agent, with a stable, non-toxic soluble fluoride compound, a buffer, one or more non-interfering carriers and no interfering phosphate compounds which will tend to precipitate calcium phosphate.

Thus, the objects of the invention include: (1) the materials employed in the invention are safe and inexpensive, (2) their methods of application are the same as those for the rinses and dentifrices and chewable tablets currently in use, but the new formulations are believed to facilitate significantly more effective prevention and reversal of dental caries.

Additionally, the present invention involves a method and materials for fluoridating teeth in situ, in a safe manner simple enough to constitute a regular part of a routine of in-home oral hygiene. The precipitation of fine calcium fluoride particles directly on the tooth surfaces accomplished by the invention is notably advantageous.

BRIEF DESCRIPTION OF THE DRAWINGS

In the description of the preferred embodiments that follows, reference will be made to the drawings comprised of the following figures:

FIG. 2 is a graph tracking the increase in turbidity (a measure of calcium fluoride formation) over time in the system of the present invention and in a NaF—$CaCl_2$ system.

DESCRIPTION OF THE PREFERRED EMBODIMENTS

Figure 1:
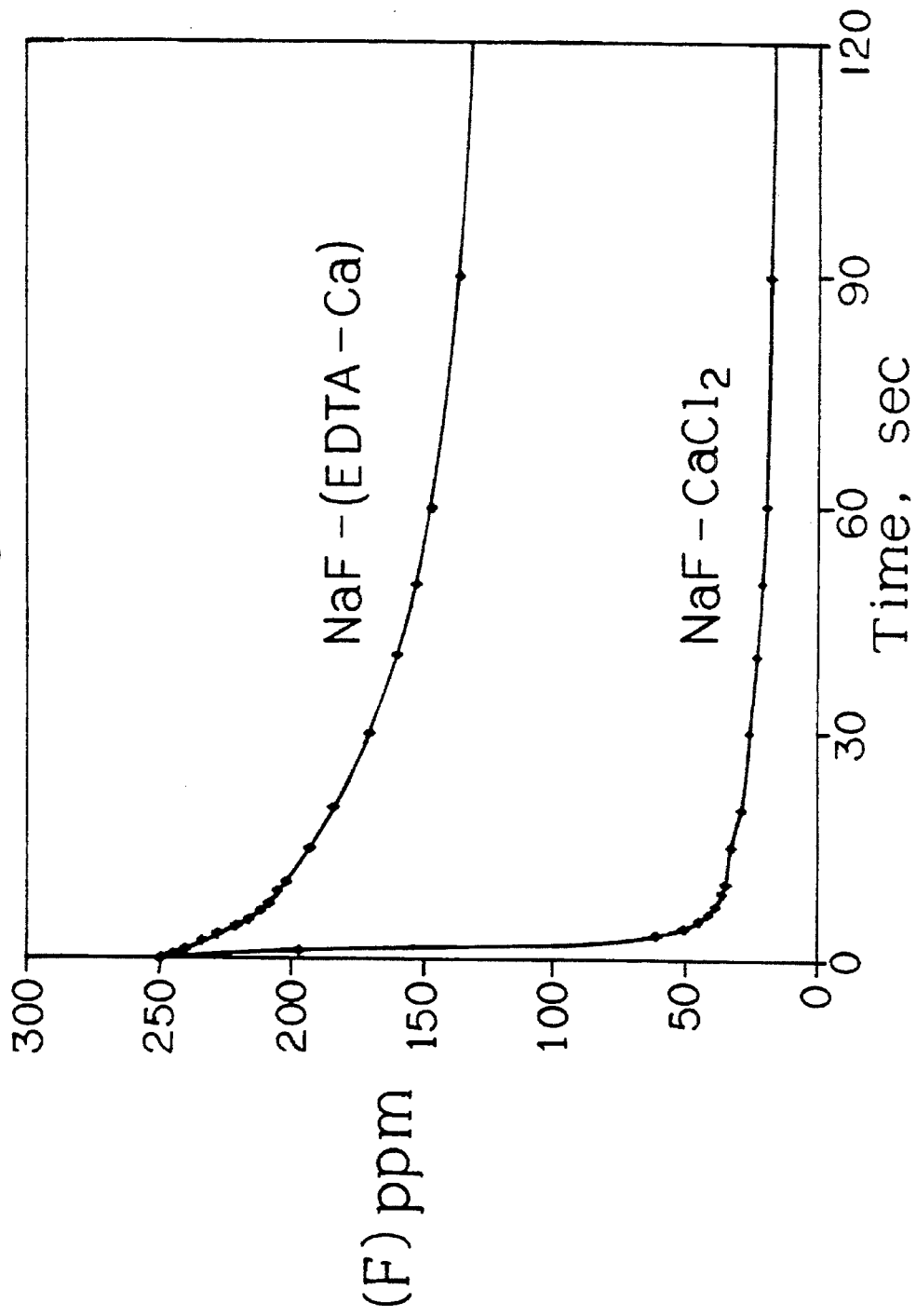
FIG. 1 is a graph tracking the decrease in fluoride concentration over time in the system of the present invention and in a NaF—$CaCl_2$ system.

The invention contemplates use of a first component comprising in part a soluble calcium salt as a source of calcium. The salt and the component overall should be non-toxic enough for oral use at the intended levels on a regular basis, and stable for the desired shelf life. Examples or appropriate calcium salts include calcium chloride, calcium acetate, calcium butylate, calcium citrate, calcium lactate, calcium salicylate, and all other non-toxic salts of calcium and inorganic or organic acids which dissolve in an aqueous solution, preferably to the extent of at least $2 \times 10^{-3}$ mol/L (approximately 0.008 grams of Ca in 100 grams of water).

The invention also contemplates the presence in the first component of a calcium complexing or chelating agent, most preferably ethylenediamine tetraacetate acid (EDTA) or one of its salts.

Ethylene diamine tetraacetic acid has four dissociable protons; the four pK's are 1.99, 2.67, 6.16, and 10.26. Thus, the dominant EDTA species in a solution is dependent on the pH of the solution as follows:

| pH | Major Species |
| --- | --- |
| below 1.99 | $EDTAH_4$ |
| from 1.99 to 2.67 | $EDTAH_3^{1-}$ |
| from 2.67 to 6.16 | $EDTAH_2^{2-}$ |
| from 6.16 to 10.26 | $EDTAH^{3-}$ |
| above 10.26 | $EDTA^{4-}$ |

It is known that $EDTA-H_4$ and $EDTA-H_3^{1-}$ do not complex $Ca^{2+}$ significantly, $EDTA-H_2^{2-}$ complexes $Ca^{2+}$ weakly, and $EDTA-H^{3-}$ and $EDTA^{4-}$ complex $Ca^{2+}$ strongly. By selecting appropriate concentrations of $CaCl_2$ and EDTA in the solution (component A) and by adjusting the pH, e.g., to 8.5 (with NaOH), the midpoint of $pK_3$ and $pK_4$, most of the Ca will be in the complexed form. When this solution is combined with a NaF and sodium acetate (NaAc)-containing solution (component B) with a pH of 4.2, half a pH unit below the pK of acetic acid, the pH of the combined solution would be reduced to 5.5, about one pH unit below the $pK_3$ of EDTA, such that the dominant EDTA species is $EDTA-H_2^{2-}$ and most of the complexed calcium is released. The free $Ca^{2+}$ can then react with F to precipitate $CaF_2$, which removes $Ca^{2+}$ ions from the solution and this, in turn, leads to the release of additional $Ca^{2+}$ from the complexed form.

Other pH-dependent Ca complexing agents that form soluble Ca complex (complex stability constant of 1 or greater) at a higher pH (5 to 14) and release some of the complexed Ca at a lower pH (3 to 10) are also contemplated for use in the invention. Suitable complexing agents such as EDTA and its salts include (trans-1,2-cyclohexylenedinitrile) tetra-acetic acid (CDTA), N-methyliminodiacetic acid (MLDA), and 1-hydroxyethan-1,1-diphosphonic acid.

The calcium component of the two-component system preferably has a pH in the range from about 5 to about 14 and may include a buffer which is an acid or a salt of an acid that has a pK value from 5 to 14 and the acid does not form insoluble calcium salts or fluoride salts. Examples of such buffers include aspartate salts (pK=9.8), glycine salts (pK=9.8), succinate salts (pK=5.6), tyrosine salts (pK=8.4), cystine salts (pK=10.3), lysine salts (pK=10.5), glycerol (pK=14.15) and HEPES (pK=7.4). For the EDTA system, the preferred buffer is a tyrosine salt. The concentration of the buffer will vary with the particular solution, but will preferably be in the range from about 0.0005 to 2 mol/L.

The invention also contemplates a second component comprising a soluble fluoride compound as a source of fluoride. Preferably, the fluoride compound is one of those approved by the FDA for use in human oral health care, such as NaF or $SnF_2$. The fluoride component of the two-component system preferably has a pH in the range from about 2 to about 11 and may also contain a buffer which is an acid or a salt of an acid that has a pK value from 2 to 11 and the acid does not form insoluble calcium or fluoride salts. Examples of such buffers include those listed above and acetate salts (pK=4.8), ascorbic salts (pK=4.1), lactic acid (pK=3.08), succinic acid (pK=5.61) and butyrate salts (pK=4.8). The concentration of the buffer will also vary with the particular solution, but will preferably be in the range from about 0.0005 to 2 mol/L. Once again, the fluoride compound and the second component overall should be non-toxic enough for oral use at the intended levels on a regular basis, and stable for the desired shelf life. Note that the first and second components may be in contact, as in a chewable tablet, provided that the product is dry until use and thus will not permit mixing of the components in an aqueous environment.

Several factors are known to affect this reaction system and consequently the effectiveness of fluoride deposition by the two-component rinse. One factor is the pH of the combined solution which increases with time as hydrogen ions are consumed by the hydrolysis. The pH of the rinse can be controlled by using different pH buffers. It is anticipated that the pH of the combined solution is controlled by the buffer(s) present in one or both components such that the pH of the combined solution is lower than the initial pH in component A, and the pH fall induces the release of calcium from the complexing agent. Another factor influencing the reaction rate is the calcium concentration, which, according to the stoichiometry of the $CaF_2$ precipitation reaction, should ideally be one half of the total F concentration. A higher calcium concentration should increase the driving force and the rate of $CaF_2$ precipitation. Thus, a higher calcium concentration relative to the fluoride concentration will be especially useful in formulations with lower Fluoride concentrations. With this principle, it is possible to increase the F deposition without increasing the fluoride concentration in the rinse or dentifrice. It is preferred that the calcium to fluoride concentration ratio of the reactive multi-component composition range from about 0.4 to about 20.

No phosphate is added to the inventive compositions, since phosphate can cause precipitation of calcium phosphate which would make less calcium available for $CaF_2$ precipitation. Additionally, phosphate is known to kinetically retard calcium fluoride formation.

The first component containing the complexed calcium and the second component containing the fluoride compound are generally mixed in an aqueous environment which may be the human mouth, or it may be a location outside the human mouth. If a location outside the human mouth is chosen to mix the first and second components, then the reactive multi-component composition should be applied to the teeth within from about 10 seconds to about 4 minutes of mixing. It is preferred that the reactive multi-component composition is applied to the mouth and teeth within about 30 seconds of the initial mixing in an aqueous environment.

The reactive multi-component composition may be contacted with the teeth for a period of time ranging from about 10 seconds to about 4 minutes or longer. However, the composition slowly becomes non-reactive, and after about 4 hours, depending on solution pH and the calcium and fluoride concentrations, the composition has lost most of its ability to precipitate fluoride on the teeth and in plaque.

The pH of the combined system may vary from about 3 to about 10. However, it is preferred that the pH of the two-component system can be from about 5 to about 9 when the system is used for formulating rinses or dentifrices that will be in direct contact with soft tissues in the mouth.

The mixing of the reactive multi-component composition may be accomplished in various ways depending on the forms in which the inventive compositions are used. The first and second components of the reactive multi-component composition will typically each contain a non-interfering carrier material. The term "non-interfering carrier material" is intended to encompass any component of the composition that does not participate in or interfere significantly with the fluoride precipitation and deposition mechanism. Examples of such non-interfering carrier materials include liquids, pastes, solids, gels and like materials or mixtures thereof. The non-interfering carrier materials may contain constituents beneficial to teeth or gums which do not react with the first or second components of the composition. Beneficial constituents might include abrasives useful in tooth cleaning, antiseptics, desensitizing agents, anesthetics, sweeteners and/or flavorings to make the composition palatable and other similar beneficial materials.

It should be noted that the non-interfering carrier material is not the calcium, fluoride, or buffer of the first and second components of the multi-component composition. In addition, calcium-containing abrasives should be avoided in the fluoride component of the invention; a silica abrasive is preferred. Calcium abrasives may react with the fluoride component leading to an uncontrolled precipitation of $CaF_2$ crystals before the fluoride component and the calcium component are mixed. This uncontrolled precipitation reduces or eliminates the fluoride available for deposition onto the teeth and plaque within the kinetics of the present multicomponent system.

Additionally, it has been found that uncontrolled instantaneous precipitation of $CaF_2$ is ineffective in producing high fluoride deposition onto the teeth. Precipitation in a $NaF-CaCl_2$ system was observed to be instantaneous, whereas that in the $Na_2SiF_6-CaCl_2$ system occurred more gradually once a calcium fluoride crystal is formed in the former solution, it is unable to attach itself on the tooth surface, to penetrate into a lesion, or to diffuse into plaque. Thus, the kinetics of the $CaF_2$ precipitation is believed to be an important factor in controlling the yield of F deposition. Thus, the aim in the inventive system has been to control the $CaF_2$ precipitation reaction so that it is not instantaneous, but occurs gradually and continuously for a period of several minutes after the two components are mixed.

Examples of forms the reactive multi-component composition might take include:

(1) For fluoride rinses, the two solutions may be contained in separate compartments in a receptacle or container or in separate receptacles or containers. Measured amounts of the two solutions are then delivered to a third compartment, preferably near the opening of a single multi-compartment receptacle (similar to the bottles used for the ACT® brand fluoride rinse). Mixing will occur as the solutions are combined in this compartment, and when the solution is swished in the mouth. The combined solution should be used within a reasonable period of time, e.g., 30 seconds, after mixing.

(2) For fluoride dentifrices, the two pastes containing the two components may be held in separate compartments in a tube or tubes similar to those used for dentifrices. Measured amounts of the two pastes will then be extruded from the tube(s) onto a tooth brush. The mixing of the two components will occur as the brushing begins.

(3) For professionally applied topical fluoride gels, either of the above two forms of packaging or an alternate form of packaging may be used depending on the consistency of the gel considered most desirable. Generally, measured amounts of the two gels are dispensed from the container(s) and mixed by stirring or spatulation. The combined gel is then placed in a tray and the tray is held tightly against the upper or lower arch of teeth for a desired period, e.g., 4 minutes.

(4) For chewable tablets, mixing will occur upon chewing and dissolution of the components in the mouth.

EXAMPLE I

Appropriate concentrations of $CaCl_2$ and EDTA are selected for the solution of component A and the pH is adjusted to 8.5 with NaOH. This solution is then combined with a NaF and sodium acetate-containing solution B with a pH of 4.2 such that the combined solution has a pH of 5.5.

Since in the present inventive system F is generally not complexed, the kinetics of calcium fluoride precipitation may be followed by measuring the decrease in [F] with a F electrode (FIG. 1). The results showed that the [F] decreased continuously over a period of 2 minutes. Turbidity measurements (a measurement of calcium fluoride formation), as recorded in FIG. 2, further showed that in the NaF-(EDTA-Ca) system the calcium fluoride precipitation occurred continuously over a period of 2 minutes. In contrast, the NaF-$CaCl_2$ system showed an instantaneous drop in [F](FIG. 1) and the calcium fluoride precipitation in the NaF-$CaCl_2$ system essentially ended after 10 seconds (FIG. 2). F uptake measurements showed that F deposition in the NaF-(EDTA-Ca) system (2.77±0.66 µg/cm$^2$) is significantly greater than that in the NaF-$CaCl_2$ system (0.40±0.18 µm/cm$^2$).

EXAMPLE II

Fluoride Rinses: A typical rinse formulation prepared and tested in accordance with the invention consists of:
solution A: 20 mmol/L in $CaCl_2$ and 10 mmol/L in EDTA; pH adjusted to 8.3 with sodium hydroxide
solution B: 24 mmol/L in NaF and 20 mmol/L in acetic acid; pH adjusted to 3.8 with sodium hydroxide
When equal volumes of A and B were mixed, the pH of the combined solution was 5.5. A constant composition fluoride titration technique (Sieck, B.; Takagi, S.; and Chow, L. C. (1990): Assessment of Loosely-bound and Firmly-bound Fluoride Uptake by Tooth Enamel from Topically Applied Fluoride Treatments, J Dent Res, 69:1261–1265) was used to measure the F deposited on tooth surfaces by the above 2-component rinse and by a NaF rinse that contained 250 ppm of F. A one-minute application of the two-component rinse deposited a mean (n=5) of 2.77±0.66 µg of F per cm$^2$ of enamel surface, which is approximately 10 times greater than the F deposition (0.24±0.09: n=3) produced by a one-minute application of the NaF rinse of the same F concentration.

EXAMPLE III

Solution A: 20 mmol/L in $CaCl_2$, 7.5 mmol/L in CDTA, pH adjusted to 11.2 with NaOH
Solution B: 24 mmol/L in NaF, 10 mmol/L in acetic acid, pH adjusted to 4.3 with NaOH
The pH of the combined solution was 6.0. The mean (n=3) F deposition was 1.36±0.01 µg/cm$^2$.

EXAMPLE IV

Solution A: 20 mmol/L in $CaCl_2$, 10 mmol/L in MLDA, pH adjusted to 10.7 with NaOH
Solution B: 24 mmol/L in NaF, 5 mmol/L in acetic acid, pH adjusted to 4.3 with NaOH
The pH of the combined solution was 8.1. The mean (n=3) F deposition was 1.28±0.24 µg/cm$^2$.

EXAMPLE V

This example shows that when neither the calcium or fluoride was complexed, the F deposition was low.
Solution A: 20 mmol/L in $CaCl_2$
Solution B: 24 mmol/L in NaF
The mean (n=3) F deposition was 0.40±0.18 µg/cm$^2$.

EXAMPLE VI

Fluoride Dentifrices: Dentifrices are chemically more complex than the rinses because they contain among other things abrasive particles, detergents, and nonaqueous liquids. However, the basic principle for precipitating calcium fluoride from a 2-component system described above for the rinses can also be applied to dentifrices. For the dentifrice formulation, the total F content is higher (1000 ppm), but the recommended quantity per application is relative lower (1 gram). A typical dentifrice formulation studied consisted of:

paste A: 100 grams of a F-free dentifrice, 0.96 grams of $CaCl_2$ and 1.47 grams of disodium ethylenediamine tetraacetate, and 0.35 grams sodium hydroxide.

paste B: 100 grams of F-free dentifrice, 0.44 grams of NaF, 0.53 grams of acetic acid, and 0.18 grams of NaOH. To assure good shelf-life, paste B should not contain soluble calcium compounds or calcium containing abrasive particles.

When equal amounts of pastes A and B are combined the total F content is 1000 ppm. The above dentifrice was used by combining 0.5 grams each of pastes A and B and brushing for 1 minute.

The constant composition fluoride titration technique was used to measure the F deposited on tooth surfaces by the above new formulation and a commercially obtained NaF containing dentifrice (1000 ppm F). The results show that a mean of 1.35±0.13 (n=3) and 0.25± µg/cm$^2$ of F were deposited by the inventive and the NaF dentifrices, respectively. The F deposition by the inventive dentifrice was more than four times that produced by the NaF dentifrice. Thus, the inventive formulation is likely to be significantly more effective.

EXAMPLE VII

Chewable fluoride supplement tablets: Chewable tablets can be formulated in a manner similar to the dentifrice of example VI. Since the tablets are packaged in a water free state, the two components described above can be safely included in the same tablet; the reaction between the calcium and complex fluoride will begin after they are in contact with the saliva through the chewing action.

EXAMPLE VIII

Fluoride Gels: Fluoride gels can be formulated to have a fluoride content similar to that of the acidulated phophate gels currently being used comercially. An example of a gel formulation consists of:

Component A: 0.6 mol/L $CaCl_2$, 0.3 mol/L EDTA, and sufficient gelling agent to form a gel pH adjusted to 8.5 with NaOH;

Component B: 0.6 mol/L NaF, 0.3 mol/L of acetic acid and sufficient gelling agent to form a gel pH adjusted to 3.8 with NaOH.

An apporopiate gelling agent in either component would be carboxyl methylcellulose; however, other gelling agents known to one skilled in the art may also be used.

As an alternative embodiment to above examples, the fluoride-containing component of the invention may be a complex fluoride as disclosed in U.S. Pat. No. 5,145,668.

The preferred embodiment of the present invention is now fully described. The above description, however, is only illustrative of the invention and is not intended to limit the invention in spirit or scope. Only the following claims and their equivalents limit the scope of the invention.

We claim:

1. A substantially phosphate-free two component system for increased deposition of fluoride onto and into dental tissue, comprising:

(a) a first component containing a soluble calcium source, a soluble calcium complexing agent having a dominant complex species at low pH which is a weaker calcium complexing agent than the dominant species at a high pH, and a buffer which is an acid or a salt of an acid that has a pK value from 5 to 14 and which acid does not form insoluble calcium salts or fluoride salts; and (b) a second component containing a fluoride compound and a buffer which is an acid or salt of an acid that has a pK value of from 2 to 11 and which acid does not form insoluble calcium or fluoride salts;

whereby when the two components are combined, the pH of the calcium component decreases sufficiently in the mixture so that the dominant complex species of the calcium complexing agent at the final pH is a weaker calcium complexing agent than the dominant species at the original pH, resulting in precipitation of calcium fluoride which removes free calcium ions from the solution leading to release of additional free calcium ions from the calcium complexing agent which, in turn, allows additional calcium fluoride to precipitate gradually and continuously over the course of about 10 seconds to about 4 minutes.

2. The system of claim 1 wherein the soluble calcium complexing agent is ethylene diamine tetraacetic acid.

3. The system of claim 1 wherein the fluoride compound is sodium fluoride.

4. The system of claim 1 wherein the fluoride compound is stannous fluoride.

5. The system of claim 1 wherein the soluble calcium source of the first component comprises a non-toxic soluble calcium salt.

6. The system of claim 5 wherein the non-toxic calcium salt is selected from the group consisting of calcium chloride, calcium acetate, calcium butylate, calcium titrate, calcium lactate, and calcium salicylate.

7. The system of claim 5 wherein the non-toxic calcium salt is characterized by solubility in an aqueous solution at a level of at least about $2 \times 10^{-3}$ mol/L.

8. The two component system of claim 1 wherein the pH of the combined solution is from about 3 to about 10.

9. The two component system of claim 8 wherein the pH of the combined solution is from about 5 to about 9.

10. A method for fluoridating teeth comprising:

(1) mixing in an aqueous environment a first component comprising a stable, non-toxic soluble calcium salt and a soluble calcium complexing agent having a dominant complex species at low pH which is a weaker calcium complexing agent than the dominant species at a high pH, and a buffer which is an acid or a salt of an acid that has a pK value from 5 to 14 and which acid does not form insoluble calcium salts or fluoride salts; with a second component comprising a stable, non-toxic soluble fluoride compound and a buffer which is an acid or salt of an acid that has a pK value of from 2 to 11 and which acid does not form insoluble calcium or fluoride salts; whereby when the two components are combined, the pH of the calcium component decreases sufficiently in the mixture so that the dominant complex species of the calcium complexing agent at the final pH is a weaker calcium complexing agent than the dominant species at the original pH, resulting in precipitation of calcium fluoride which removes free calcium ions from the solution leading to release of additional free calcium ions from the calcium complexing agent which, in turn, allows additional calcium fluoride to precipitate gradually and continuously over the course of about 10 seconds to about 4 minutes; and (2) promptly applying the mixture to tooth surfaces.

11. A substantially phosphate-free two component system for increased deposition of fluoride onto and into dental tissue, comprising:

(a) a first component containing a soluble calcium source and a soluble calcium complexing agent having a dominant complex species at low pH which is a weaker calcium complexing agent than the dominant species at a high pH, and a buffer which is an acid or a salt of an acid that has a pK value from 5 to 14 and which acid does not form insoluble calcium salts or fluoride salts, in a first non-interfering carrier; and (b) a second component containing a fluoride compound and a buffer which is an acid or salt of an acid that has a pK value of from 2 to 11 and which acid does not form insoluble calcium or fluoride salts, in a second non-interfering carrier;

whereby when the two components are combined, the pH of the calcium component decreases sufficiently in the mixture so that the dominant complex species of the calcium complexing agent at the final pH is a weaker calcium complexing agent than the dominant species at the original pH, resulting in precipitation of calcium fluoride which removes free calcium ions from the solution leading to release of additional free calcium ions from the calcium complexing agent which, in turn, allows additional calcium fluoride to precipitate gradually and continuously over the course of about 10 seconds to about 4 minutes.

12. The two component system of claim 11 wherein the pH of the combined solution is from about 3 to about 10.

13. The two component system of claim 11 wherein the soluble calcium complexing agent is ethylene diamine tetraacetic acid.

14. The two component system of claim 11 wherein the first and second non-interfering carriers are the same.

15. The system of claim 14 wherein the non-interfering carriers are selected from the group consisting of a mouth rinse, a dentifrice, a gel, and a chewable tablet.

16. The two component system of claim 11 wherein the first and second non-interfering carriers are selected from the group consisting of a mouth rinse, a dentifrice, a gel, and a chewable tablet.

17. The two component system of claim 11 wherein the concentration of the first buffer is in the range of 0.0005 to 2 mol/L.

18. The two component system of claim 11 wherein the first buffer is selected from the group consisting of HEPES, tyrosine, glycine, aspartic acid, cystine, lysine, glycerol and salts that form these acids.

19. The two component system of claim 11 wherein the concentration of the second buffer is in the range of 0.0005 to 2 mol/L.

20. The two component system of claim 11 wherein the second buffer is selected from the group consisting of lactic acid, ascorbic acid, acetic acid, butyric acid, succinic acid, HEPES, glycine, aspartic acid, cystine and salts that form these acids.

21. The two component system of claim 11 wherein the pH of the combined solution is from about 5 to about 9.

22. The two component system of claim 11 wherein the fluoride compound is sodium fluoride.

23. The two component system of claim 11 wherein the fluoride compound is stannous fluoride.

24. A substantially phosphate-free two component system for increased deposition of fluoride onto and into dental tissue, comprising:

(a) a first non-phosphate containing component containing a non-toxic soluble calcium salt, ethylene diamine tetraacetic acid, and a buffer which is an acid or a salt of an acid that has a pK value from 5 to 14 and which acid does not form insoluble calcium salts or fluoride salts, in a first non-interfering carrier; and (b) a second non-phosphate containing component containing a fluoride compound and a buffer which is an acid or salt of an acid that has a pK value of from 2 to 11 and which acid does not form insoluble calcium or fluoride salts, in a second non interfering carrier;

whereby when the two components are combined, precipitation of calcium fluoride removes free calcium ions from the solution leading to the release of additional free calcium ions from the calcium complexing agent which, in turn, allows additional calcium fluoride to precipitate gradually and continuously over the course of about 10 seconds to about 4 minutes.

25. The two component system of claim 24 wherein the fluoride compound is sodium fluoride.

26. The two component system of claim 24 wherein the fluoride compound is stannous fluoride.

27. The two component system of claim 24 wherein the non-toxic calcium salt is selected from the group consisting of calcium chloride, calcium acetate, calcium butylate, calcium titrate, calcium lactate, and calcium salicylate.

28. The two component system of claim 24 wherein the pH of the first component is from about 8.3 to about 11.2 and the pH of the second component is from about 3.8 to about 4.3.

29. The two component system of claim 24 wherein the pH of the combined solution is from about 3 to about 10.

30. The two component system of claim 24 wherein the pH of the combined solution is from about 5 to about 9.

* * * * *